(12) United States Patent
Molt et al.

(10) Patent No.: US 9,108,998 B2
(45) Date of Patent: Aug. 18, 2015

(54) DINUCLEAR PLATINUM-CARBENE COMPLEXES AND THE USE THEREOF IN OLEDS

(75) Inventors: Oliver Molt, Weinheim (DE); Christian Lennartz, Schifferstadt (DE); Gerhard Wagenblast, Wachenheim (DE); Thomas Strassner, Dresden (DE); Yvonne Unger, Dresden (DE)

(73) Assignee: BASF SE, Ludwigshafen (DE)

( * ) Notice: Subject to any disclaimer, the term of this patent is extended or adjusted under 35 U.S.C. 154(b) by 798 days.

(21) Appl. No.: 13/501,492

(22) PCT Filed: Oct. 13, 2010

(86) PCT No.: PCT/EP2010/065330
§ 371 (c)(1),
(2), (4) Date: Apr. 12, 2012

(87) PCT Pub. No.: WO2011/045337
PCT Pub. Date: Apr. 21, 2011

(65) Prior Publication Data
US 2012/0199823 A1    Aug. 9, 2012

Related U.S. Application Data

(60) Provisional application No. 61/251,320, filed on Oct. 14, 2009.

(51) Int. Cl.
| | | |
|---|---|---|
| *H01L 51/54* | (2006.01) | |
| *C09K 11/06* | (2006.01) | |
| *C07F 15/00* | (2006.01) | |
| *H01L 51/00* | (2006.01) | |
| *H05B 33/14* | (2006.01) | |
| *H01L 51/50* | (2006.01) | |

(52) U.S. Cl.
CPC ............ *C07F 15/0086* (2013.01); *C09K 11/06* (2013.01); *H01L 51/009* (2013.01); *H01L 51/0087* (2013.01); *H05B 33/14* (2013.01); *C09K 2211/1044* (2013.01); *C09K 2211/1048* (2013.01); *C09K 2211/1059* (2013.01); *C09K 2211/185* (2013.01); *H01L 51/5016* (2013.01); *Y02E 10/549* (2013.01)

(58) Field of Classification Search
CPC ............ C07F 15/0086; H01L 51/0084; H01L 51/0087; H01L 51/009; H01L 51/50; H01L 51/5016; C09K 11/06; C09K 2211/1044; C09K 2211/1059; C09K 2211/1074; C09K 2211/185; H05B 33/14; Y02E 10/549
See application file for complete search history.

(56) References Cited

U.S. PATENT DOCUMENTS

2005/0260446 A1*  11/2005  Mackenzie et al. ........... 428/690
2008/0018221 A1    1/2008  Egen et al.
2009/0018330 A1    1/2009  Molt et al.
2009/0079329 A1*   3/2009  Murakami et al. ............ 313/504
2010/0213824 A1    8/2010  Adler et al.

FOREIGN PATENT DOCUMENTS

| WO | 00 70655 | 11/2000 |
|---|---|---|
| WO | 2004 093210 | 10/2004 |
| WO | 2005 019373 | 3/2005 |
| WO | 2005 113704 | 12/2005 |
| WO | 2006 056418 | 6/2006 |
| WO | 2007 088093 | 8/2007 |
| WO | 2008141637 | 11/2008 |
| WO | 2009 003898 | 1/2009 |

OTHER PUBLICATIONS

Haneder et al. "Controlling the radiative rate of deep-blue electrophosphorescent organometallic complexes by singlet-triplet gap engineering." Adv. Mater. 2008, vol. 20, pp. 3325-3330.*
International Search Report issued on Jan. 12, 2011 in PCT/EP10/065330 filed on Oct. 13, 2010.
Lai, S.W., et al., "Synthesis of Organoplatinum Oligomers by Employing N-Donor Bridges with Predesigned Geometry: Structural and Photophysical Properties of luminescent Cyclometallated Platinum(II), Macrocycles", Organometallics, vol. 18, No. 20, pp. 3991-3997, XP-002615229. (Aug. 28, 1999).
Stylianides, N., et al., "Cyclometalated and Alkoxyphenyl-Substituted Palladium Imidazolin-2-ylidene Complexes. Synthetic, Structural, and Catalytic Studies", Organometallics, vol. 26, No. 23, pp. 5627-5635, XP-002615230. (Oct. 2, 2007).
Baldo, M.A., et al., "Very high efficiency green organic light-emitting devices based on electrophsphorescence", Applied Physics Letters., vol. 75, No. 1., pp. 4-6 (Jul. 5, 1999).
Koshiyama, T., et al., "Redox-controlled Luminescence of a Cyclometalated Dinuclear Platinum Complex Bridged with Pyridine-2-thiolate Ions", Chemistry Letters, vol. 33, No. 10, pp. 1386-1387. (2004).
Saito, K., et al., "Organic Light-Emitting Diodes Based on a Binuclear Platinum (II) Complex", Japanese Journal of Applied Physics, Part 2, Letters & Express Letters, vol. 44, No. 16, pp. L500-L501. (2005).
Tanabe, M., et al., "Ligand Exchange of Diplatinum Complex with Bridging Silyl Ligands Involving Si—H Bond Cleavage and Formation", Organometallics, vol. 27, No. 10, pp. 2258-2267. (2008).
Ma, B., et al., "Synthetic Control of Pt—Pt Separation and Photophysics of Binuclear Platinum Complexes", J. Am. Chem. Soc., vol. 127, No. 1, pp. 28-29. (2005).

(Continued)

*Primary Examiner* — Michael H Wilson
(74) *Attorney, Agent, or Firm* — Oblon, McClelland, Maier & Neustadt, L.L.P.

(57) ABSTRACT

The present invention relates to dinuclear Pt-carbene complexes comprising carbene ligands and pyrazole bridges, to a process for preparing the dinuclear Pt-carbene complexes by contacting suitable Pt compounds with the corresponding ligands or ligand precursors and/or pyrazole or corresponding pyrazole derivatives, to organic electronic components comprising at least one such dinuclear Pt-carbene complex, to an OLED comprising at least one such dinuclear Pt-carbene complex, to a light-emitting layer comprising at least one such dinuclear Pt-carbene complex, to an OLED comprising such a light-emitting layer, to a device selected from the group consisting of stationary visual display units, mobile visual display units and illumination means, comprising such an OLED, and to the use of an inventive dinuclear Pt-carbene complex in OLEDs.

18 Claims, No Drawings

(56) References Cited

OTHER PUBLICATIONS

Qi., X., et al., "Evidence for enhanced dipolar interactions between Pt centers in binuclear phosphorescent complexes", Chemical Physical Letters, vol. 458, pp. 323-328. (2008).

Ma, B., et al., "Platinum Binuclear Complexes as Phosphorescent Dopants for Monochromatic and White Organic Light-Emitting Diodes", Advanced Functional Materials, vol. 16, pp. 2438-2446. (2006).

Chang, S.-Y., et al., "Blue-Emitting Platinum (II) Complexes Bearing both Pyridylpyrazolate Chelate and Bridging Pyrazolate Ligands: Synthesis, Structures, and Photophysical Properties", Inorganic Chemistry, vol. 46, No. 26, pp. 11202-11212. (2007).

Jain, V. K., et al., "Binuclear Pyrazolato-bridged Platinum (II) Complexes: Synthesis, Characterization and Crystal Structure", J. Chem. Soc. Dalton Trans., pp. 3625-3628. (1993).

Hill, M. N. S., "Reactivity of Co-ordinated Ligands, Part VII. Reactions of Diene Complexes of Palladium (II) and Platinum (II) with Carboxylic Acids", J. Chem. Soc. (A), pp. 2341-2347. (1971).

Powell, J., et al., "Conformational Studies of Bridging Carboxylate Complexes of Palladium (II) and Platinum (II)", Inorganic Chemistry, vol. 11, No. 5, pp. 1039-1048. (1972).

U.S. Appl. No. 14/123,530, filed Dec. 3, 2013, Koenemann, et al.

U.S. Appl. No. 14/115,934, filed Nov. 6, 2013, Wagenblast, et al.

U.S. Appl. No. 13/516,117, filed Aug. 27, 2012, Molt, et al.

\* cited by examiner

DINUCLEAR PLATINUM-CARBENE COMPLEXES AND THE USE THEREOF IN OLEDS

The present invention relates to dinuclear Pt-carbene complexes, to organic light-emitting diodes (OLEDs) comprising at least one such dinuclear Pt-carbene complex, to light-emitting layers comprising at least one such dinuclear Pt-carbene complex, a device, for example stationary or mobile visual display units or illumination means, comprising a corresponding OLED, and to the use of the inventive dinuclear Pt-carbene complexes in OLEDs, for example as emitters, matrix materials, charge transport materials and/or charge blockers.

Organic electronics is a subfield of electronics and uses electronic circuits which comprise polymers or smaller organic compounds. Fields of use of organic electronics are the use of polymers or smaller organic compounds in organic light-emitting diodes (OLEDs) or light-emitting electrochemical cells (LEEC), use in organic solar cells (organic photovoltaics) and in switching elements such as organic transistors, for example organic FETs and organic TFTs.

The use of suitable novel organic materials thus allows various new types of components based on organic electronics to be provided, such as displays, sensors, transistors, memory or photovoltaic cells. This makes possible the development of components for new applications which are thin, light, flexible and producible at low cost.

A preferred field of use according to the present invention is the use of the inventive compounds in organic light-emitting diodes.

Organic light-emitting diodes (OLEDs) exploit the property of materials of emitting light when these materials are excited by electrical current. OLEDs are of particular interest as an alternative to cathode ray tubes and liquid-crystal displays for producing flat visual display units. Owing to the very compact design and the intrinsically low power consumption, the device comprising OLEDs is suitable especially for mobile applications, for example for applications in cellphones, laptops, etc., and for illumination.

The basic principles of the way in which OLEDs work and suitable structures (layers) of OLEDs are specified, for example, in WO 2005/113704 and the literature cited therein. The light-emitting materials (emitters) used may, as well as fluorescent materials (fluorescence emitters), be phosphorescent materials (phosphorescence emitters). The phosphorescence emitters are typically organometallic complexes which, in contrast to the fluorescence emitters which exhibit singlet emission, exhibit triplet emission (M. A. Baldo et al., Appl. Phys. Lett. 1999, 75, 4-6). For quantum-mechanical reasons, when the phosphorescence emitters are used, up to four times the quantum efficiency, energy efficiency and power efficiency is possible.

Of particular interest are organic light-emitting diodes with long operative lifetime, good efficiency, high stability to thermal stresses and a low use and operating voltage.

The prior art discloses various chemical compounds which can perform different tasks within an OLED.

WO 2004/093210 A1 discloses organic light-emitting diodes (OLEDs) which have dinuclear metal compounds as emitter materials. Light-emitting diodes which have an anode, a cathode and an emitting layer between anode and cathode are disclosed. The emitting layer comprises an emitter material which has more than one metal center. The dinuclear compounds according to WO 2004/093210 preferably comprise two metal centers, each metal center being attached to at least one bridging ligand. Suitable bridging ligands according to this document are five- or six-membered rings which have nitrogen as a heteroatom. In addition, pyrazole is mentioned as a bridging ligand. In addition to the bridging ligands, the dinuclear complexes according to this document comprise further ligands, though no carbene ligands are disclosed in WO 2004/093210.

T. Koshijama et al., Chem. Lett. Vol. 33, 10, 2004, 1386-1387 disclose cyclometallated dinuclear platinum complexes which are bridged by means of pyridine-2-thiolate ions. On application of an electric voltage, these complexes have luminescence. The document cited does not disclose dinuclear platinum complexes which have bridging pyrazole units or ligands which are attached to the platinum atoms via carbene bonds.

Saito et al., Jpn. J. Appl. Phys. 2005, 44, L500-L501 disclose an OLED with a dinuclear cyclometallated platinum complex with a pyridinethiolate bridge. The document does not disclose dinuclear platinum complexes with bridging pyrazole units or carbene-metal bonds.

Lai et al., Organometallics 1999, 18, 3991-3997 disclose pyrazole-bridged cyclometallated platinum complexes and the quantum yields thereof, but there are no carbene bonds to the metal.

M. Tanabe et al., Organometallics 2008, 27, 2258 to 2267, disclose dinuclear platinum complexes with bridging silyl ligands. Firstly, no complexes which comprise platinum atoms bridged via pyrazole units are disclosed. In addition, no Pt-carbene complexes are disclosed.

WO 2008/141637 A2 discloses phosphorescent metal complexes, radiation-emitting components which comprise such a phosphorescent metal complex, and a process for preparing the compounds mentioned. In addition to mononuclear metal complexes, dinuclear platinum complexes are also disclosed. In general, pyrazole is disclosed as a possible ligand for corresponding complexes. However, it is not disclosed that pyrazole is a bridging ligand between platinum atoms, or that further ligands attached to the metal atom(s) via carbene bonds are present in addition to the bridging pyrazole ligands.

B. Ma et al., J. Am. Chem. Soc. 2005, 127, 28 to 29, disclose dinuclear platinum complexes which have pyrazole units as bridging ligands between the two platinum atoms. The complexes of this document do not have any ligands attached to the metal centers via carbene bonds.

Qi et al., Chem. Phys. Lett. 2008, 458, 323-328 and Ma et al., Adv. Funct. Mater. 2006, 16, 2438-2446 disclose further studies regarding the dinuclear complexes presented in Ma et al., J. Am. Chem. Soc. 2005, 127, 28-29.

S.-Y. Chang et al., *Inorg. Chem.* 2007, 46, 11202-11212 disclose blue light-emitting platinum(II) complexes comprising firstly pyridylpyrazole ligands, and secondly chelating pyrazole ligands. Corresponding complexes in which two platinum cations are bridged with pyrazole or pyrazole derivatives are not disclosed.

Jain et al., J. Chem. Soc. Dalton Trans. 1993, 3625-3628 disclose pyrazole-bridged compounds. However, these are not cyclometallated and there are no photoluminescence data.

Hill et al., Inorg. Phys. Theor. 1971, 2341-2347 disclose dinuclear metal complexes which comprise palladium or platinum cations. The two metal cations are bridged via carboxylates of organic carboxylic acids. As further ligands, the complexes according to Hill et al. comprise dienes.

Powell et al., Inorg. Chem. 1972, 11, 1039-1048 disclose dinuclear complexes which comprise palladium or platinum as metal cations. The two metal cations are bridged to one another via carboxyl groups. The complexes mentioned bear diphenylphosphine groups as further ligands.

The dinuclear platinum complexes disclosed in the prior art have the disadvantage that, when these complexes are used as emitters in organic light-emitting diodes, only inadequate quantum yields are possible. In addition, properties needed specifically for use in organic light-emitting diodes, for example efficiency and stability, of the dinuclear platinum complexes cited in the prior art are in need of improvement.

It is therefore an object of the present invention to provide further materials suitable for use in organic light-emitting diodes and further applications in organic electronics. More particularly, phosphorescence emitters for use in OLEDs shall be provided. In addition, the materials should be suitable for providing OLEDs which ensure good efficiencies, good operative lifetimes and a high stability to thermal stress, and a low use and operating voltage of the OLEDs.

These objects are achieved in accordance with the invention by a dinuclear Pt-carbene complex of the general formula (Ia) or (Ib) or isomers thereof

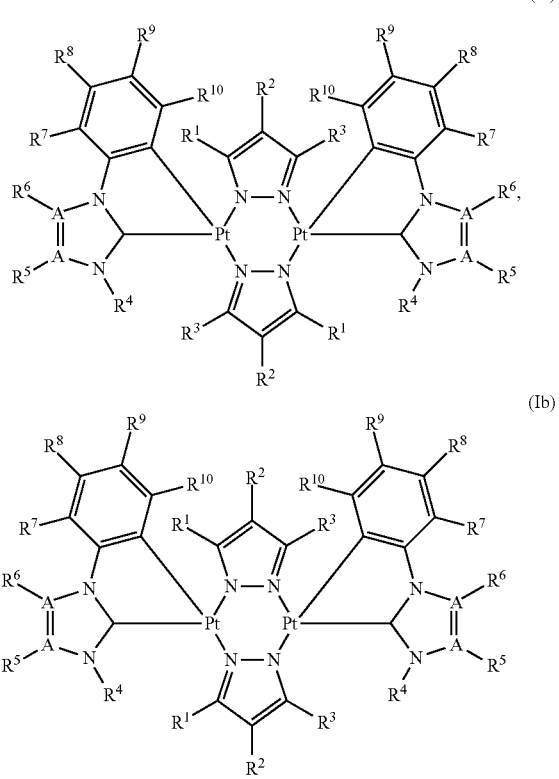

where A, $R^1$, $R^2$, $R^3$, $R^4$, $R^5$, $R^6$, $R^7$, $R^8$ and $R^9$ and $R^{10}$ are each defined as follows:

A is independently N or C, $R^1$, $R^2$, $R^3$ are each independently hydrogen, a linear or branched alkyl radical having 1 to 20 carbon atoms, optionally interrupted by at least one heteroatom and optionally bearing at least one functional group, cycloalkyl radical having 3 to 20 carbon atoms, $R^4$ is independently a linear or branched alkyl radical having 1 to 20 carbon atoms, optionally interrupted by at least one heteroatom and optionally bearing at least one functional group, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, $R^5$, $R^6$ are each independently a free electron pair if A is N or, if A is C, hydrogen, linear or branched alkyl radical having 1 to 20 carbon atoms, optionally interrupted by at least one heteroatom and optionally bearing at least one functional group, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, or $R^4$ and $R^5$ or $R^5$ and $R^6$ form, together with N and A or with A and A, a saturated, unsaturated or aromatic ring having a total of 5 to 18 carbon atoms and/or heteroatoms, optionally interrupted by at least one further heteroatom, $R^7$, $R^8$, $R^9$, $R^{10}$ are each independently hydrogen, a linear or branched alkyl radical having 1 to 20 carbon atoms, optionally interrupted by at least one heteroatom and optionally bearing at least one functional group, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, functional group selected from ether, amino, thio, ester, carbonyl, nitro or halogen group, or $R^7$ and $R^8$ or $R^8$ and $R^9$ or $R^9$ and $R^{10}$ together form a saturated, unsaturated or aromatic, optionally substituted ring having a total of 5 to 18 carbon atoms and/or heteroatoms, optionally interrupted by at least one heteroatom, and/or $R^6$ and $R^7$ together form a saturated or unsaturated, linear or branched bridge having a total of 1 to 30 carbon atoms and/or heteroatoms, optionally comprising heteroatoms, aromatic units, heteroaromatic units and/or functional groups, and to which a substituted or unsubstituted, five- to eight-membered ring comprising carbon atoms and/or heteroatoms is optionally fused.

The general formulae (Ia) and (Ib) are two possible isomers of the inventive dinuclear Pt-carbene complexes. These inventive dinuclear Pt-carbene complexes may additionally be present in all isomers known to those skilled in the art, for example the following isomers of the general formulae (Ic) and (Id)

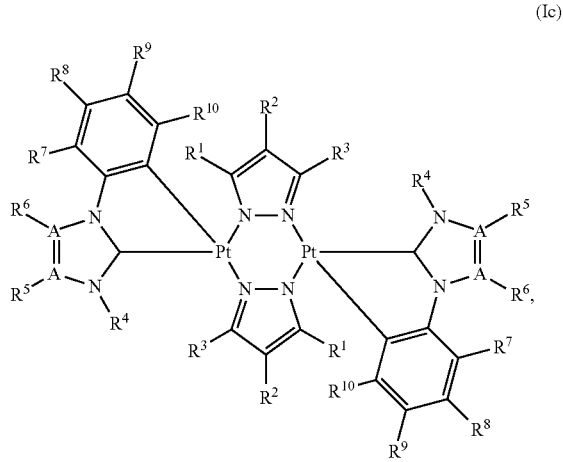

(Id)

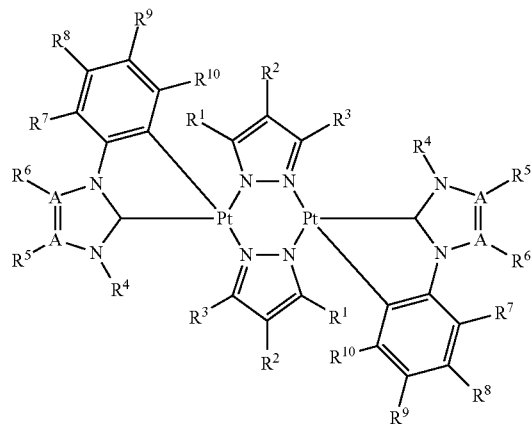

According to the invention, the isomers of the dinuclear Pt-carbene complexes mentioned may be present as individual compounds or as mixtures of two or more of the possible isomers.

In the context of the present invention, the terms aryl radical or group, heteroaryl radical or group and alkyl radical or group are each defined as follows:

An aryl radical or group is understood to mean a radical with a base skeleton of 6 to 30 carbon atoms, preferably 6 to 18 carbon atoms, which is formed from one aromatic ring or a plurality of fused aromatic rings. Suitable base skeletons are, for example, phenyl, benzyl, naphthyl, anthracenyl or phenanthrenyl. This base skeleton may be unsubstituted, which means that all carbon atoms which are substitutable bear hydrogen atoms, or substituted at one, more than one or all substitutable positions of the base skeleton. Suitable substituents are, for example, alkyl radicals, preferably alkyl radicals having 1 to 8 carbon atoms, more preferably methyl, ethyl, i-propyl or t-butyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear a double bond, more preferably alkenyl radicals with one double bond and 1 to 8 carbon atoms, or groups with donor or acceptor action. Groups with donor action are understood to mean groups which have a +I and/or +M effect, and groups with acceptor action are understood to mean groups which have a −I and/or −M effect. Suitable groups with donor or acceptor action are halogen radicals, preferably F, Cl, Br, more preferably F, alkoxy radicals, aryloxy radicals, carbonyl radicals, ester radicals, amine radicals, amide radicals, $CH_2F$ groups, $CHF_2$ groups, $CF_3$ groups, CN groups, thio groups or SCN groups. The aryl radicals most preferably bear substituents selected from the group consisting of methyl, F, amine, thio group and alkoxy, or the aryl radicals are unsubstituted. The aryl radical or the aryl group is preferably a $C_6$-aryl radical which is optionally substituted by at least one of the aforementioned substituents. The $C_6$-aryl radical more preferably has none, one, two or three of the aforementioned substituents. The aryl radicals present in accordance with the invention more preferably do not have substituents.

A heteroaryl radical or a heteroaryl group are understood to mean radicals which differ from the aforementioned aryl radicals in that at least one carbon atom in the base skeleton of the aryl radicals is replaced by a heteroatom. Preferred heteroatoms are N, O and S. Most preferably, one or two carbon atoms of the base skeleton of the aryl radicals are replaced by heteroatoms. The base skeleton is especially preferably selected from pyridyl, pyrimidyl, pyrazyl, triazyl, and five-membered heteroaromatics such as pyrrole, furan, thiophene, pyrazole, imidazole, triazole, oxazole, thiazole. The base skeleton may be substituted at none, one, more than one or all substitutable positions of the base skeleton. Suitable substituents are the same as have already been mentioned for the aryl groups.

An alkyl radical or an alkyl group is understood to mean a radical having 1 to 20 carbon atoms, preferably 1 to 10 carbon atoms, more preferably 1 to 8 carbon atoms. This alkyl radical may be branched or unbranched and optionally be interrupted by one or more heteroatoms, preferably N, O or S. In addition, this alkyl radical may be substituted by one or more of the substituents mentioned for the aryl groups. It is likewise possible that the alkyl radical bears one or more aryl groups. All of the aryl groups listed above are suitable. The alkyl radicals are more preferably selected from the group consisting of methyl, ethyl, i-propyl, n-propyl, i-butyl, n-butyl, t-butyl, sec-butyl, i-pentyl, n-pentyl, sec-pentyl, neopentyl, n-hexyl, i-hexyl and sec-hexyl. Very particular preference is given to methyl, i-propyl, tert-butyl and n-hexyl, especially methyl.

A cycloalkyl radical or a cycloalkyl group is understood to mean a cyclic radical having 3 to 20 carbon atoms, preferably 3 to 10 carbon atoms, more preferably 3 to 8 carbon atoms. This cycloalkyl radical may optionally be interrupted by one or more heteroatoms, preferably N, O or S. In addition, this cycloalkyl radical may be unsubstituted or substituted, i.e. substituted by one or more of the substituents mentioned for the aryl groups. It is likewise possible that the cycloalkyl radical bears one or more aryl groups. All of the aryl groups listed above are suitable.

According to the invention, the statements made for the aryl, heteroaryl, alkyl and cycloalkyl radicals apply independently to the $R^1$, $R^2$, $R^3$, $R^4$, $R^5$, $R^6$, $R^7$, $R^8$, $R^9$ and $R^{10}$ radicals, where $R^5$ and $R^6$, in the case that A is N, are each a free electron pair, which means that no substituent selected from the abovementioned group is present on these ring nitrogen atoms. In the case that A is C, $R^5$ and $R^6$ are each independently hydrogen and/or the substituents mentioned.

In a further embodiment of the dinuclear Pt-carbene complexes of the general formula (Ia) or (Ib), $R^4$ and $R^5$ or $R^5$ and $R^6$ together with N and A or with A and A form a saturated, unsaturated or aromatic ring having a total of 5 to 18 carbon atoms and/or heteroatoms, optionally interrupted by at least one further heteroatom, or $R^7$ and $R^8$ or $R^8$ and $R^9$ together form a saturated, unsaturated or aromatic, optionally substituted ring having a total of 5 to 30 carbon atoms and/or heteroatoms, optionally interrupted by at least one heteroatom.

In this context, according to the present invention, "a total of" means that the ring atoms A are also counted. According to the invention, only the $R^4$ and $R^5$ or $R^5$ and $R^6$ or $R^7$ and $R^8$ or $R^8$ and $R^9$ radicals form corresponding rings which are present in the same five-membered or six-membered ring.

In a preferred embodiment, $R^7$ and $R^8$ together form a saturated, unsaturated or aromatic ring having a total of 5 to 30 carbon atoms and/or heteroatoms, optionally interrupted by at least one heteroatom. For example, $R^7$ and $R^8$ form a ring system of the following formula (IIa) or (IIb)

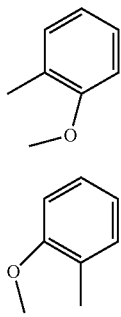
(IIa)

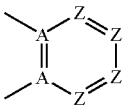
(IIb)

In a further preferred embodiment, $R^5$ and $R^6$ together with A and A form a ring system of the general formula (IIc)

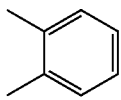
(IIc)

where Z is independently CR' or N, where R' is hydrogen, linear or branched alkyl radical having 1 to 20 carbon atoms, optionally interrupted by at least one heteroatom and optionally bearing at least one functional group, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, functional group selected from ether, amino, thio, ester, carbonyl, nitro or halogen group.

In a particularly preferred embodiment, $R^6$ and $R^7$ form a phenyl ring, corresponding to the formula (IId)

(IId)

The dinuclear Pt-carbene complexes of the general formula (Ia) or (Ib) comprise two platinum atoms. In the inventive dinuclear Pt-carbene complexes of the general formula (Ia) or (Ib), the platinum atoms are present in the +II oxidation state.

In a particularly preferred embodiment of the inventive Pt-carbene complexes of the general formula (Ia) or (Ib), A, $R^1$, $R^2$, $R^3$, $R^4$, $R^5$, $R^6$, $R^7$, $R^8$, and $R^9$ and $R^{10}$ are each defined as follows:

A is independently N or C,
$R^1$, $R^3$ are each independently hydrogen, a linear or branched alkyl radical having 1 to 4 carbon atoms,
$R^2$ is hydrogen,
$R^4$ is independently a linear or branched alkyl radical having 1 to 4 carbon atoms, substituted or unsubstituted aryl radical having 6 carbon atoms, substituted or unsubstituted heteroaryl radical having 5 carbon atoms and/or heteroatoms,
$R^5$, $R^6$ are each a free electron pair if A is N or, if A is C, each independently hydrogen, a linear or branched alkyl radical having 1 to 4 carbon atoms, substituted or unsubstituted aryl radical having 6 carbon atoms, substituted or unsubstituted heteroaryl radical having 5 carbon atoms and/or heteroatoms, or $R^5$ and $R^6$ together with A and A form an aromatic ring having a total of 5 to 10 carbon atoms and/or heteroatoms, optionally interrupted by at least one further heteroatom,
$R^7$, $R^8$, $R^9$, $R^{10}$ are independently hydrogen or
$R^7$ and $R^8$ together form an unsaturated or aromatic, optionally substituted ring having a total of 5 to 12 carbon atoms and/or heteroatoms, optionally interrupted by at least one heteroatom.

In a very particularly preferred embodiment of the present invention, the inventive dinuclear Pt-carbene complexes correspond to the following formulae (Ia), (Ib), (Ic), (Id), (Ie) or (If) or isomers thereof:

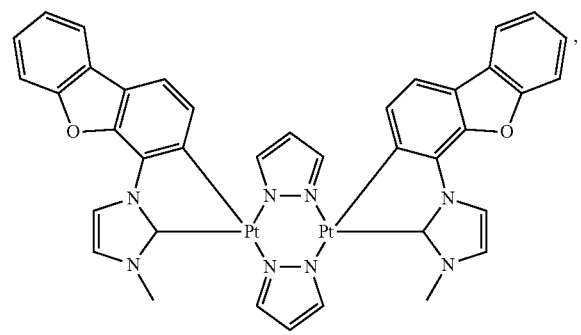
(Ia)

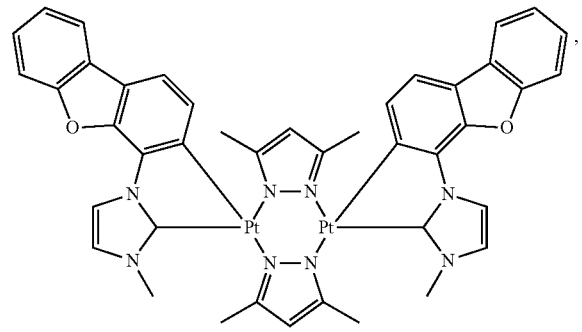
(Ib)

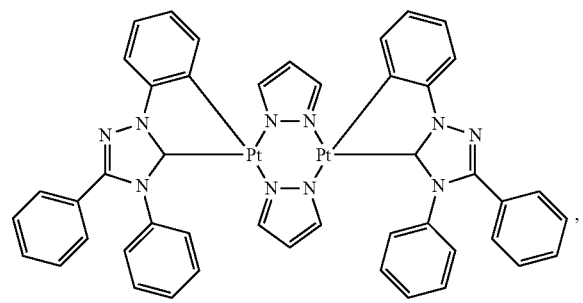
(Ic)

-continued (Id)

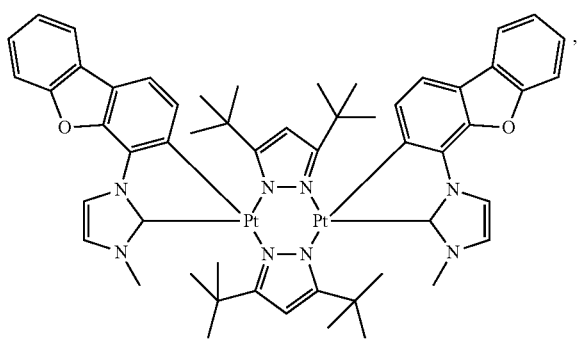

(Ie)

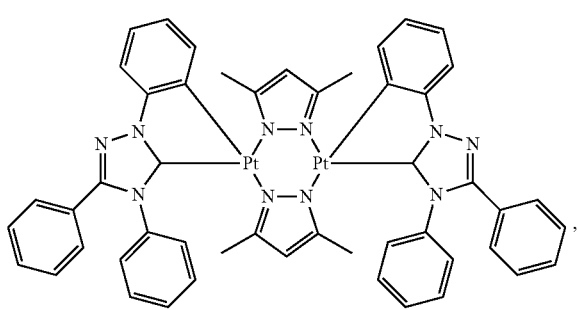

(If)

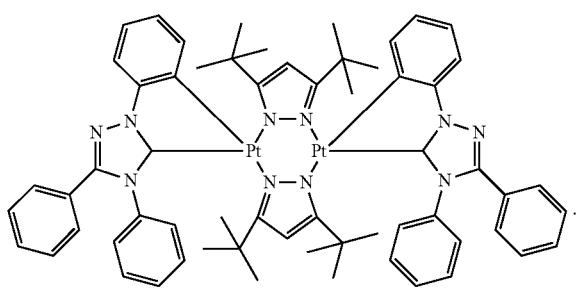

The aforementioned dinuclear Pt-carbene complexes and mixtures thereof are outstandingly suitable as emitter molecules in organic light-emitting diodes (OLEDs). By variations of the ligands, it is possible to provide corresponding complexes which exhibit electroluminescence in the red, green and especially in the blue region of the electromagnetic spectrum. The uncharged Pt-carbene complexes used in accordance with the invention are therefore suitable for use in industrially usable full-color displays or white OLEDs as illumination means.

The present invention also relates to a process for preparing the inventive dinuclear Pt-carbene complexes by contacting suitable Pt compounds with the corresponding ligands or ligand precursors and/or pyrazole or corresponding pyrazole derivatives.

In principle, the process according to the invention for preparing the Pt-carbene complexes of the general formula (Ia) or (Ib) can be effected in two embodiments.

In the first embodiment (variant A) of the process according to the invention, suitable Pt compounds, i.e. salts or complexes, are reacted with suitable ligand precursors and pyrazole or corresponding pyrazole derivatives.

In general, suitable Pt salts are all of those which are known to those skilled in the art and exhibit a sufficiently high reactivity under the inventive reaction conditions. Preference is given to corresponding Pt salts or complexes selected from the group consisting of $Pt(COD)Cl_2$ (COD=cyclooctadiene), $Pt(PPh_3)_2Cl_2$, $Pt(pyridine)_2Cl_2$, $Pt(phenanthroline)Cl_2$, $Pt(NH_3)_2Cl_2$, $Pt(acac)_2$, $PtCl_2$, $K_2PtCl_4$ and mixtures thereof, particular preference being given to using $Pt(COD)Cl_2$.

Suitable ligand precursors are compounds which, after reaction with Pt compounds and pyrazole or derivatives thereof, give rise to the dinuclear Pt-carbene complexes of the general formula (Ia) or (Ib). In a preferred embodiment, correspondingly suitable ligand precursors of the general formula (III)

(III)

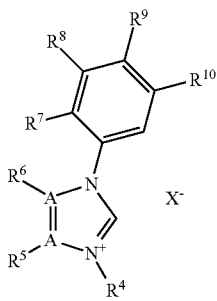

in which $R^4$, $R^5$, $R^6$, $R^7$, $R^8$, $R^9$, $R^{10}$ and A are each as defined for formula (Ia) or (Ib). It is clear to the person skilled in the art that the $R^4$, $R^5$, $R^6$, $R^7$, $R^8$, $R^9$, $R^{10}$ and A radicals have to be selected such that the desired compound of the general formula (Ia) or (Ib) is obtained.

In the compound of the general formula (III), $X^-$ is, for example, halide, especially chloride, bromide, iodide, more preferably iodide, or $BF_4^-$, $PF_6^-$, $SbF_6^-$, $ClO_4^-$, ½ $SO_4^-$, preferably $BF_4^-$, $PF_6^-$.

Particularly preferred compounds of the general formula (III) which are used as ligand precursors in the process according to the invention are those compounds which comprise the abovementioned preferred $R^4$, $R^5$, $R^6$, $R^7$, $R^8$, $R^9$, $R^{10}$ and A radicals, and in which $X^-$ is $I^-$, most preferably the following compounds (IIIa) and (IIIb):

(IIIa)

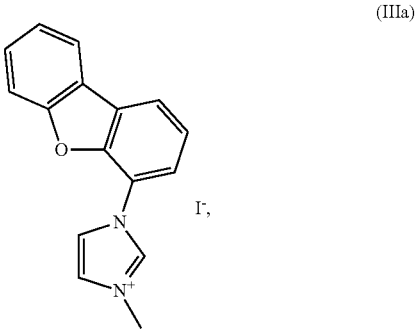

(IIIb)

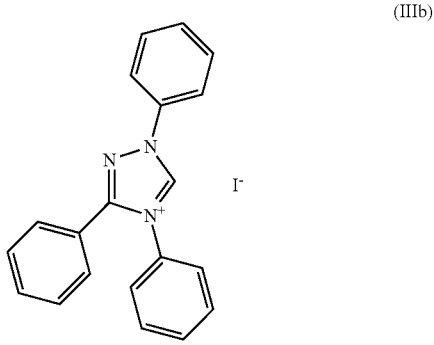

Corresponding compounds of the general formulae (IIIa) and (IIIb) are obtainable by processes known to the person skilled in the art.

According to the invention, pyrazole and corresponding derivatives are of the general formula (IV1) or (IV2):

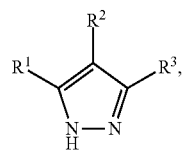
(IV1)

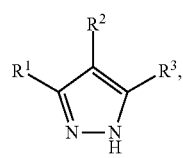
(IV2)

where pyrazole may occur in two tautomeric forms (IV1) and (IV2). For all compounds of the general formula (IV), in accordance with the invention, both tautomeric forms 1 and 2 shall be encompassed in each case.

In the general formulae (IV1) and (IV2), $R^1$, $R^2$ and $R^3$ each have the abovementioned definitions and preferred definitions. It is clear to the person skilled in the art that the $R^1$, $R^2$ and $R^3$ radicals should be selected such that the desired compound of the general formula (Ia) or (Ib) is obtained.

Particularly preferred compounds of the general formula (IV) which are used in the process according to the invention are the following compounds (IVa), (IVb), (IVc), (IVd), (IVe) and (IVf), where the tautomeric forms are also encompassed in each case:

(IVa)

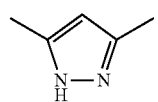
(IVb)

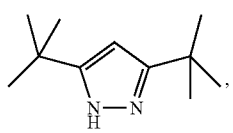
(IVc)

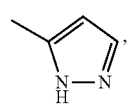
(IVd)

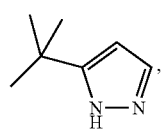
(IVe)

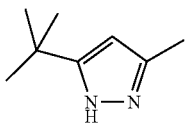
(IVf)

Corresponding compounds of the general formula (IV) are obtainable by processes known to the person skilled in the art or are commercially available.

The molar ratio of the compounds used in this embodiment of the process according to the invention is preferably such that corresponding compounds of the general formula (Ia) or (Ib) are obtained, for example 1 to 10 eq, preferably 1 to 5 eq, more preferably 1 to 2 eq, of ligand, 1 eq of metal, and 1 to 10 eq, preferably 1 to 5 eq, more preferably 2 to 4 eq, of pyrazole or pyrazole derivative.

The reaction is effected generally at a temperature of 0 to 150° C., preferably 0 to 120° C., for example room temperature, 100° C. or 115° C.

Preference is given to performing the process according to the invention in a solvent. Suitable solvents are known to those skilled in the art, for example ethers, cyclic ethers, ketones, polar solvents, preferably dioxane, butanone, ethoxyethanol, dimethylformamide (DMF) or mixtures thereof.

The reaction time depends on the desired Pt-carbene complex and is generally 1 to 80 hours, preferably 2 to 70 hours, more preferably 10 to 60 hours, for example 54 hours.

The resulting Pt-carbene complex of the general formula (Ia) or (Ib) can be worked up by methods known to those skilled in the art. For example, the product precipitated during the reaction is filtered, optionally washed, for example with water, and then purified by column chromatography with dichloromethane and dried.

In a second embodiment (variant B), the inventive dinuclear Pt-carbene complexes can be obtained by reacting Pt complexes in which the ligands present in the corresponding compounds of the general formula (Ia) or (Ib) are present with pyrazole or corresponding derivatives thereof.

Pt complexes in which the ligands present in the corresponding desired compounds of the general formula (Ia) or (Ib) are present correspond, in a preferred embodiment, to the following general formula (V):

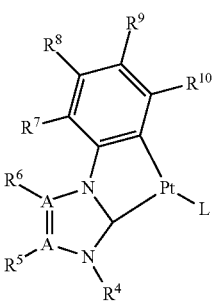
(V)

in which $R^4$, $R^5$, $R^6$, $R^7$, $R^8$, $R^9$, $R^{10}$ and A each have the abovementioned definitions and preferred definitions. It is clear to the person skilled in the art that the $R^4$, $R^5$, $R^6$, $R^7$, $R^8$, $R^9$, $R^{10}$ and A radicals should be selected such that the desired compound of the general formula (Ia) or (Ib) is obtained.

In the general formula (V), L represents one or more mono- or polydentate ligands which are bonded to the Pt in the compound of the general formula (V). Suitable ligands which are eliminated readily during the reaction with pyrazole or the pyrazole derivative under the inventive reaction conditions are known to those skilled in the art, for example cyclooctadiene (cod), Cl, Br, acetylacetonate (acac), 1,3-diketiminates (nacnac), OAc (acetate), $BF_4$, $PF_6$, $PPh_3$ or solvents.

L is more preferably a bidentate ligand of the following formula (VI):

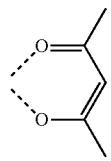

(VI)

where bonds to the Pt atom are via the dotted bonds.

Pyrazole or corresponding pyrazole derivatives usable in this process according to the invention are the abovementioned compounds of the general formula (IV).

In this embodiment of the process according to the invention, the molar ratio of the compounds used is preferably such that corresponding compounds of the general formula (Ia) or (Ib) are obtained, for example 1 eq of complex and 1 to 10 eq, preferably 1 to 5 eq, more preferably 1 to 2 eq, of pyrazole or pyrazole derivative.

The reaction is effected generally at a temperature of 0 to 150° C., preferably 0 to 120° C., for example 60° C.

The process according to the invention is preferably performed in a solvent. Suitable solvents are known to those skilled in the art, for example ethers, cyclic ethers, ketones, polar solvents, preferably methylene chloride, dioxane, ethoxyethanol, butanone, dimethylformamide (DMF) or mixtures thereof.

The reaction time depends on the desired Pt-carbene complex and is generally 1 to 50 hours, preferably 2 to 40 hours, more preferably 10 to 30 hours, for example 24 hours.

The dinuclear Pt-carbene complexes of the general formula (Ia) or (Ib) thus obtained can be worked up as already described for the first embodiment, preference being given to column chromatography purification with dichloromethane.

The inventive dinuclear Pt-carbene complexes of the general formula (Ia) or (Ib) are outstandingly suitable as emitter substances since they have an emission (electroluminescence) in the visible region of the electromagnetic spectrum, for example at 440 to 500 nm. By virtue of the dinuclear Pt-carbene complexes, it is possible to provide compounds which have electroluminescence in the red, green and in the blue region of the electromagnetic spectrum. It is thus possible, with the aid of the inventive dinuclear Pt-carbene complexes as emitter substances, to provide technically usable full-color displays or white OLEDs for illumination means.

In addition, the inventive compounds of the general formula (Ia) or (Ib) have very high quantum yields, 60 to 100%. The quantum yield is determined by processes known to those skilled in the art, for example by UV/Vis spectroscopy of the emitters in solution or in thin polymer films.

The present application therefore further provides an OLED comprising at least one inventive dinuclear Pt-carbene complex of the general formula (Ia) or (Ib).

The present application further also provides for the use of the dinuclear Pt-carbene complexes of the general formula (Ia) or (Ib) as a light-emitting layer in OLEDs, preferably as an emitter, matrix material, charge transport material and/or charge blocker.

In principle, organic light-emitting diodes are formed from a plurality of layers:
Anode (1)
Hole-transporting layer (2)
Light-emitting layer (3)
Electron-transporting layer (4)
Cathode (5)

The dinuclear Pt-carbene complexes of the general formula (Ia) or (Ib) are preferably used in the light-emitting layer (3) as emitter molecules.

The present application therefore further provides a light-emitting layer comprising at least one of the inventive dinuclear Pt-carbene complexes of the general formula (Ia) or (Ib), preferably as an emitter molecule. Preferred dinuclear Pt-carbene complexes of the general formula (Ia) or (Ib) have already been mentioned above.

The dinuclear Pt-carbene complexes of the general formula (Ia) or (Ib) used in accordance with the invention may be present in the light-emitting layer in substance, i.e. without further additions. However, it is also possible that, in addition to the dinuclear Pt-carbene complexes of the general formula (Ia) or (Ib) used in accordance with the invention, further compounds are present in the light-emitting layer. For example, a fluorescent dye may be present in order to alter the emission color of the dinuclear Pt-carbene complex used as the emitter molecule. In addition, a diluent material (matrix material) may be used. This diluent material may be a polymer, for example poly(N-vinylcarbazole) or polysilane. The diluent material may, however, likewise be a small molecule, for example 4,4'-N,N'-dicarbazolebiphenyl (CDP) or tertiary aromatic amines. When a diluent material is used, the proportion of the dinuclear Pt-carbene complexes used in accordance with the invention in the light-emitting layer is generally less than 40% by weight, preferably 3 to 20% by weight.

The inventive dinuclear Pt-carbene complexes of the general formula (Ia) or (Ib) are preferably used in a matrix material. The light-emitting layer thus preferably comprises at least one inventive dinuclear Pt-carbene complex of the general formula (Ia) or (Ib) and a matrix material.

The present application further provides a light-emitting layer comprising at least one dinuclear Pt-carbene complex of the general formula (Ia) or (Ib) as an emitter molecule. Preferred complexes of the general formula (Ia) or (Ib) have already been mentioned above.

The individual layers among the aforementioned layers of the OLED may in turn be formed from two or more layers. For example, the hole-transporting layer may be formed from one layer, into which holes are injected from the electrode, and a layer which transports the holes away from the hole-injecting layer into the light-emitting layer. The electron-transporting layer may likewise consist of a plurality of layers, for example of a layer in which electrons are injected through the electrode, and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the dinuclear Pt-carbene complexes according to the present invention used as emitter substances in accordance with the invention.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer. The further layers in the OLED may be formed from any material which is typically used in such layers and is known to those skilled in the art.

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole transport materials for the layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole transport material. Customarily used hole-transporting molecules are selected from the group consisting of 4,4'-bis[N-(1-naphthyl)-N-phenylamino]biphenyl (NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB) and porphyrin compounds such as copper phthalocyanines. Customarily used hole-transporting polymers are selected from the group consisting of polyvinylcarbazoles, (phenylmethyl) polysilanes and polyanilines. It is likewise possible to obtain hole-transporting polymers by doping hole-transporting molecules into polymers such as polystyrene and polycarbonate. Suitable hole-transporting molecules are the molecules already mentioned above.

Suitable electron-transporting materials for the layer (4) of the inventive OLEDs comprise metals chelated with oxinoid compounds, such as tris(8-hydroxyquinolato)aluminum ($Alq_3$), compounds based on phenanthroline such as 2,9-dimethyl-4,7-diphenyl-1,10-phenanthroline (DDPA) or 4,7-diphenyl-1,10-phenanthroline (DPA) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds or LiF may be applied between the organic layer and the cathode in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:
  a hole injection layer between the anode (1) and the hole-transporting layer (2);
  a blocking layer for electrons between the hole-transporting layer (2) and the light-emitting layer (3);
  a blocking layer for holes between the light-emitting layer (3) and the electron-transporting layer (4);
  an electron injection layer between the electron-transporting layer (4) and the cathode (5).

Those skilled in the art know how suitable materials have to be selected (for example on the basis of electrochemical investigations). Suitable materials for the individual layers are known to those skilled in the art and disclosed, for example, in WO 00/70655.

In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed.

In general, the different layers have the following thicknesses: anode (2) 500 to 5000 Å, preferably 1000 to 2000 Å; hole-transporting layer (3) 50 to 1000 Å, preferably 200 to 800 Å; light-emitting layer (4) 10 to 1000 Å, preferably 100 to 800 Å; electron-transporting layer (5) 50 to 1000 Å, preferably 200 to 800 Å; cathode (6) 200 to 10 000 Å, preferably 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

The inventive OLEDs may be used in all devices in which electroluminescence is useful. Suitable devices are preferably selected from stationary and mobile visual display units. The present invention therefore also relates to a device selected from the group consisting of stationary visual display units and mobile visual display units, comprising an inventive OLED.

Stationary visual display units are, for example, visual display units of computers, televisions, visual display units in printers, kitchen appliances and advertising panels, illuminations and information panels. Mobile visual display units are, for example, visual display units in cellphones, laptops, vehicles and destination displays on buses and trains.

In addition, the inventive dinuclear Pt-carbene complexes of the general formula (Ia) or (Ib) may be used in OLEDs with inverse structure. The inventive complexes are preferably used in these inverse OLEDs in turn in the light-emitting layer, more preferably as a light-emitting layer without further additives. The structure of inverse OLEDs and the materials customarily used therein are known to those skilled in the art.

The present invention also relates to an organic electronic component comprising at least one inventive dinuclear Pt-carbene complex of the general formula (Ia) or (Ib). The present invention more preferably relates to a corresponding organic electronic component which is an organic light-emitting diode (OLED), organic photovoltaic cell (OPV), organic field-effect transistor (OFET) or light-emitting electrochemical cell (LEEC).

EXAMPLES

The following compounds according to the present invention are synthesized and photophysically characterized by the general method below.

The dinuclear Pt carbene complexes mentioned in the following may be present as single isomers (single compounds) or as mixtures of two or more of the possible isomers. In the following, one isomer is shown in each case. However, this does not exclude that the respective compound is present in form of more than one isomer.

The photoluminescence of the emitting complexes is carried out in thin PMMA films (polymethyl methacrylate) with an emitter doping level of 2%. The films are produced as follows: 2 mg/l of emitter are dissolved in a 10% PMMA solution in DCM (Mw 120 kD) and applied to a microscope slide with a 60 μm doctor blade. The excitation is effected at a wavelength of 325 nm (HeCd laser) at right angles to the microscope slide, and the emission is detected at an angle of 45° by means of fiber optics in the diode array spectrometer.

General Experimental Procedure:

Variant A:

0.8 mmol of the appropriate imidazolium salt (corresponding to formula III) and 0.4 mmol of silver(I) oxide (0.093 g) are stirred in 20 ml of dry dioxane at room temperature under argon for 16 hours. After adding 10 ml of butanone and 0.8 mmol of cyclooctadieneplatinum dichloride (0.299 g), the reaction mixture is stirred under reflux for 16 hours. The mixture is concentrated to dryness and taken up in 20 ml of dimethylformamide, and 3.2 mmol of pyrazole or pyrazole derivative and 3.2 mmol of potassium tert-butoxide (0.359 g) are added. The reaction mixture is stirred at room temperature for 16 hours and at 100° C. for 6 hours. The solvent is removed and the residue is washed with water. Subsequently, the crude product is purified by column chromatography (G60 silica gel, dichloromethane).

Variant B:

0.26 mmol of the cyclometallated platinum(II) acetylacetonate complex (corresponding to formula V) is refluxed with 0.26 mmol of pyrazole or pyrazole derivative and 0.26 mmol of sodium methoxide (0.014 g) in 10 ml of dichloromethane under argon for 24 hours. Once the solvent has been removed, the crude product is purified by column chromatography (G60 silica gel, dichloromethane).

Di-[1-(dibenzofuranyl)-3-methylimidazol-2-ylidene-C2,C2']platinum(II) dipyrazolate(compound Ia'))

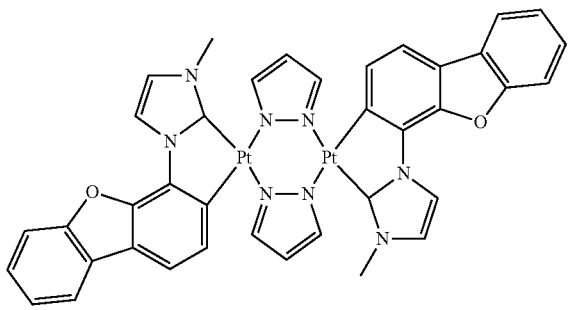

0.8 mmol of 1-(dibenzofuranyl)-3-methylimidazolium iodide (0.301 g) and 3.2 mmol of pyrazole (0.218 g) react according to variant A.

Empirical formula: $C_{38}H_{28}N_8O_2Pt_2$
Molar mass: 1018.840 g/mol
Yield: 0.168 g (41.2% of theory)
Melting point: decomposition at >357° C.

$^1$H NMR (ppm, $d_6$-DMSO, 300.13 MHz):
δ=8.11-7.95 (m, 6H, CH); 7.72-7.60 (m, 6H, CH); 7.48-7.45 (m, 4H, CH); 7.39-7.31 (m, 6H, CH); 3.30 (s, 6H, NCH$_3$)

$^{13}$C NMR (ppm, CDCl$_3$, 75.475 MHz):
δ=154.98 (Cipso); 141.98 (Cipso); 139.25 (CH); 137.89 (CH); 132.61 (Cipso); 130.69 (Cipso); 128.43 (CH); 126.82 (CH); 124.04 (Cipso); 123.24 (CH); 123.10 (CH); 121.42 (Cispo); 120.41 (CH); 117.40 (CH); 116.26 (CH); 111.62 (CH); 105.40 (CH); 35.67 (NCH$_3$)

Elemental analysis for $C_{38}H_{28}N_8O_2Pt_2$:

|  | C | H | N |
| --- | --- | --- | --- |
| calculated | 44.79% | 2.77% | 11.00% |
| found | 44.49% | 2.57% | 10.53% | or:

0.26 mmol of [1-(dibenzofuranyl)-3-methylimidazol-2-ylidene-C2,C2']platinum(II) acetyl-acetonate (0.142 g) reacts with 0.26 mmol of pyrazole (0.018 g) according to variant B.

Empirical formula: $C_{38}H_{28}N_8O_2Pt_2$
Molar mass: 1018.840 g/mol
Yield: 0.118 g (89.1% of theory)

QY=73%
λem=471 nm, 505 nm

Di-[1,3,5-triphenyl-1,3,4-triazol-2-ylidene-C2,C2'] platinum(II) dipyrazolate (compound Ic'))

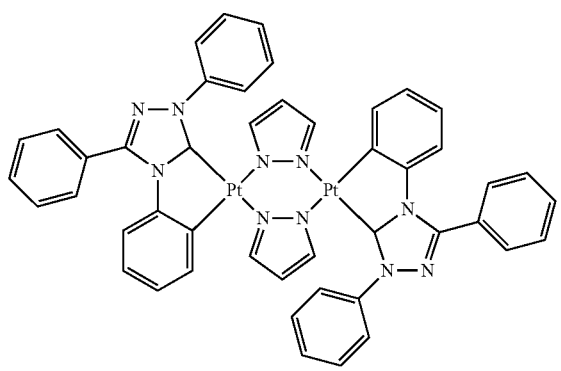

0.8 mmol of 1,3,5-triphenyl-1,3,4-triazolium iodide (0.340 g) and 3.2 mmol of pyrazole (0.218 g) react according to variant A.
Empirical formula: $C_{46}H_{34}N_{10}Pt_2$
Molar mass: 1116.988 g/mol
Yield: 0.063 g (14.1% of theory)
Melting point: decomposition at >320° C.
$^1$H NMR (ppm, $d_6$-DMSO, 300.13 MHz):
δ=8.02 (d, 2H, J=7.6 Hz, CH); 7.59-7.27 (m, 32H, CH)
$^{13}$C NMR (ppm, $d_6$-DMSO, 75.475 MHz):
δ=151.20 (Cipso); 145.40 (Cipso); 137.58 (Cipso); 133.20 (Cipso); 130.40 (CH); 129.41 (CH); 129.17 (CH); 129.07 (CH); 128.58 (CH); 128.05 (CH); 128.02 (CH); 126.17 (Cipso); 125.41 (CH); 118.30 (CH)
QY=63.7%
λem=444 nm, 473 nm

Di-[4(4-bromophenyl)-3-methylimidazol-2-ylidene-C2,C2']platinum(II) dipyrazolate

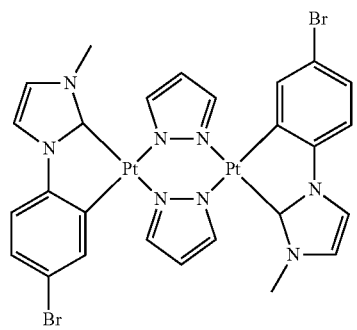

0.8 mmol of (4-bromophenyl)-3-methylimidazolium iodide (0.292 g) and 3.2 mmol of pyrazole (0.218 g) react according to variant A.
Empirical formula: $C_{26}H_{22}N_8Pt_2Br_2$
Molar mass: 996.480 g/mol
Yield: 0.181 g (45.4% of theory)
Melting point: decomposition at >340° C.
$^1$H NMR (ppm, $d_6$-DMSO, 300.13 MHz):
δ=7.91 (d, 2H, J=2.1 Hz, CH); 7.75 (d, 2H, J=2.0 Hz, CH); 7.62 (d, 2H, J=1.9 Hz, CH); 7.33-7.25 (m, 4H, CH); 7.20 (d, 2H, J=2.0 Hz, CH); 7.11 (d, 2H, J=2.1 Hz, CH); 6.38 (t, 2H, J=2.0 Hz, CH); 3.21 (s, 6H, NCH$_3$)
$^{13}$C NMR (ppm, $d_6$-DMSO, 75.475 MHz):
δ=156.23 (Cipso); 146.90 (Cipso); 139.30 (CH); 137.44 (CH); 135.69 (CH); 135.45 (Cipso); 125.61 (CH); 122.93 (CH); 116.88 (Cipso); 115.73 (CH); 112.95 (CH); 105.69 (CH); 35.38 (CH$_3$)
QY=8%
λem=429 nm, 453 nm

Di-[(4(4-methoxyphenyl)-3-methylimidazol-2-ylidene-C2,C2']platinum(II) dipyrazolate

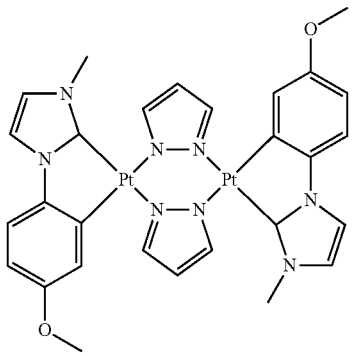

0.8 mmol of (4-methoxyphenyl)-3-methylimidazolium iodide (0.253 g) and 3.2 mmol of pyrazole (0.218 g) react according to variant A.
Empirical formula: $C_{28}H_{28}N_8Pt_2O_2$
Molar mass: 898.740 g/mol
Yield: 0.040 g (11.1% of theory)
Melting point: decomposition at >320° C.
$^1$H NMR (ppm, $d_6$-DMSO, 300.13 MHz):
δ=7.83 (d, 2H, J=1.8 Hz, CH); 7.80 (d, 2H, J=1.8 Hz, CH); 7.75 (d, 2H, J=1.8 Hz, CH); 7.70 (s, 2H, CH); 7.62 (d, 2H, J=1.5 Hz, CH); 7.21-7.16 (m, 4H, CH); 6.53 (d, 2H, J=8.4 Hz, CH); 6.34 (s, 2H, CH); 3.70 (s, 6H, OCH$_3$); 3.16 (s, 6H, NCH$_3$)
$^{13}$C NMR (ppm, d6-DMSO, 125 MHz):
δ=167.06 (Cipso-O); 155.88 (Cipso); 141.47 (Cipso); 139.12 (CH); 137.57 (CH); 133.64 (Cipso); 122.33 (CH); 120.23 (CH); 115.28 (CH); 111.33 (CH); 106.64 (CH); 105.30 (CH); 54.75 (OCH$_3$); 35.44 (NCH$_3$)
QY=36%
λem=441 nm, 466 nm

Di-[(4-methylphenyl)-3-methylimidazol-2-ylidene-C2,C2']platinum(II) dipyrazolate

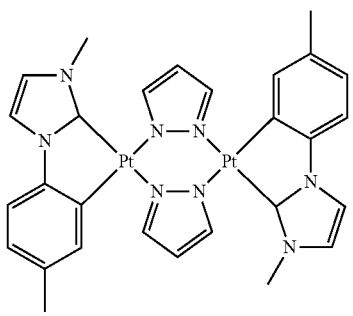

0.8 mmol of (4-methylphenyl)-3-methylimidazolium iodide (0.240 g) and 3.2 mmol of pyrazole (0.218 g) react according to variant A.
Empirical formula: $C_{28}H_{28}N_8Pt_2$
Molar mass: 866.740 g/mol
Yield: 0.018 g (5.2% of theory)
Melting point: decomposition at >300° C.
$^1$H NMR (ppm, $d_6$-DMSO, 300.13 MHz):
δ=7.82 (d, 2H, J=1.9 Hz, CH); 7.69 (d, 2H, J=1.8 Hz, CH); 7.60 (d, 2H, J=1.7 Hz, CH); 7.19 (d, 2H, J=1.7 Hz, CH); 7.13 (d, 2H, J=7.7 Hz, CH); 6.89 (s, 2H, CH); 6.77 (d, 2H, J=7.6 Hz, CH); 6.34 (s, 2H, CH); 3.17 (s, 6H, NCH$_3$); 2.15 (s, 6H, CH$_3$)
$^{13}$C NMR (ppm, $d_6$-DMSO, 75.475 MHz):
δ=156.71 (Cipso); 145.43 (Cipso); 138.88 (CH); 134.67 (CH); 132.48 (Cipso); 131.72 (Cipso); 123.27 (CH); 122.28 (CH); 115.23 (CH); 110.49 (CH); 105.20 (CH); 35.29 (NCH$_3$); 21.14 (CH$_3$)
QY=31%
λem=428 nm, 453 nm Di-[(4-nitrophenyl)-3-methylimidazol-2-ylidene-C2,C2']platinum(II) dipyrazolate

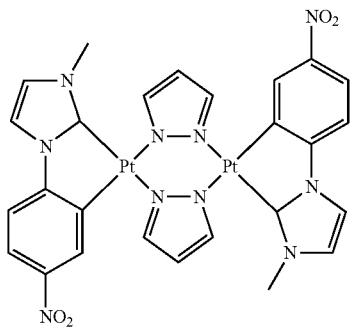

0.8 mmol of (4-nitrophenyl)-3-methylimidazolium iodide (0.265 g) and 3.2 mmol of pyrazole (0.218 g) react according to variant A.
Empirical formula: $C_{26}H_{22}N_{10}O_4Pt_2$
Molar mass: 928.692 g/mol
Yield: 0.060 g (16.2% of theory)
Melting point: decomposition at >340° C.
$^1$H NMR (ppm, $d_6$-DMSO, 300.13 MHz):
δ=8.13 (d, 2H, J=9.1 Hz, CH); 8.03 (d, 2H, J=1.5 Hz, CH); 8.94 (dd, 2H, J=8.5 Hz, CH); 7.82 (s, 2H, CH); 7.71 (s, 2H, CH); 7.53 (d, 2H, J=8.5 Hz, CH); 7.30 (d, 2H, J=1.3 Hz, CH); 6.45 (s, 2H, CH); 3.24 (s, 6H, NCH$_3$)
$^{13}$C NMR (ppm, d6-DMSO, 125 MHz):
δ=157.58 (Cipso); 153.38 (Cipso); 143.70 (Cipso); 142.82 (CH); 133.87 (Cipso); 128.64 (CH); 127.55 (CH); 125.42 (CH); 120.48 (CH); 118.45 (CH); 109.39 (CH); 106.00 (CH); 35.54 (NCH$_3$)

Di-[1-(dibenzofuranyl)-3-methylimidazol-2-ylidene-C2,C2']platinum(II) di-3,5-dimethylpyrazolate (compound (Ib'))

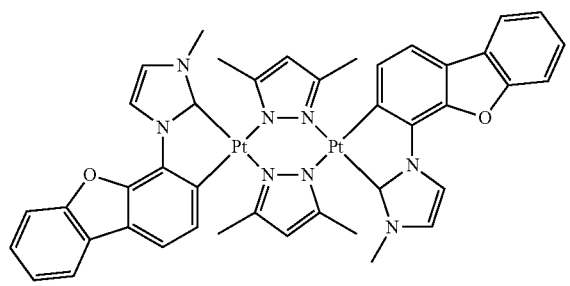

0.8 mmol of 1-(dibenzofuranyl)-3-methylimidazolium iodide (0.301 g) and 3.2 mmol of 3,5-dimethylpyrazole (0.308 g) react according to variant A.
Empirical formula: $C_{42}H_{36}N_8O_2Pt_2$
Molar mass: 1074.944 g/mol
Yield: 0.026 g (6.1% of theory)
Melting point: 221.6° C.
$^1$H NMR (ppm, $d_6$-DMSO, 300.13 MHz):
δ=8.03 (d, 2H, J=2.0 Hz; CH); 7.99 (d, 2H, J=7.2 Hz, CH); 7.66 (d, 2H, J=8.1 Hz, CH); 7.59 (d, 2H, J=7.5 Hz, CH); 7.47 (t, 2H, J=7.0 Hz, CH); 7.35 (t, 2H, J=7.6 Hz, CH); 7.34 (d, 2H, J=2.0 Hz, CH); 7.04 (d, 2H, J=7.8 Hz, CH); 6.01 (s, 2H, CH); 3.40 (s, 6H, NCH$_3$); 2.25 (s, 6H, CH$_3$); 2.20 (s, 6H, CH$_3$)
$^{13}$C NMR (ppm, $d_6$-DMSO, 125 MHz):
δ=155.06 (Cipso); 145.45 (Cipso); 142.09 (Cipso); 130.84 (Cipso); 129.31 (CH); 126.78 (CH); 124.14 (Cipso); 123.28 (CH); 122.92 (CH); 121.15 (Cispo); 120.40 (CH); 117.63 (CH); 116.26 (CH); 111.67 (CH); 104.20 (CH); 34.83 (NCH3); 14.00 (CH$_3$); 13.80 (CH$_3$)
QY=85%
λem=472 nm, 506 nm Di-[1-(dibenzofuranyl)-3-methylimidazol-2-ylidene-C2,C2']platinum(II) di-3,5-dimethylpyrazolate (compound Id'))

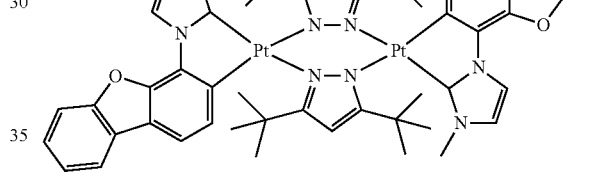

0.8 mmol of 1-(dibenzofuranyl)-3-methylimidazolium iodide (0.301 g) and 3.2 mmol of 3,5-di-tert-butylpyrazole (0.577 g) react according to variant A.
Empirical formula: $C_{54}H_{60}N_8O_2Pt_2$
Molar mass: 1243.256 g/mol
Yield: 0.115 g (23.1% of theory)
Melting point: 244° C.
$^1$H NMR (ppm, $d_6$-DMSO, 300.13 MHz):
δ=7.96 (d, 2H, J=7.4 Hz; CH); 7.89 (d, 2H, J=2.0 Hz, CH); 7.61-7.52 (m, 4H, CH); 7.45-7.32 (m, 6H, CH); 7.20-7.18 (m, 2H, CH); 6.29 (s, 2H, CH); 3.33 (s, 6H, NCH3); 1.44 (s, 18H, CH$_3$); 1.41 (s, 18H, CH$_3$)
$^{13}$C NMR (ppm, $d_6$-DMSO, 125 MHz):
δ=158.67 (Cipso); 154.86 (Cipso); 141.51 (Cipso); 133.42 (Cipso); 130.95 (CH); 130.00 (Cipso); 126.52 (CH); 124.08 (Cipso); 123.09 (CH); 122.34 (CH); 120.57 (Cispo); 120.22 (CH); 117.09 (CH); 115.05 (CH); 111.47 (CH); 101.10 (CH); 35.91 (NCH$_3$); 32.37 (CH$_3$); 31.29 (CH$_3$)
QY=50%
λem=512 nm Preparation of OLEDs The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer, AJ20-1000 from Plexcore, is spun on from solution.

Diode Example 1

After the hole injection layer, the organic materials specified below are applied by vapor deposition at a rate of approx. 0.5-5 nm/min to the clean substrate at about $10^{-7}$-$10^{-9}$ mbar. As hole conductor and exciton blocker Ir(DPBIC)$_3$ is applied in a thickness of 20 nm, of which the first 10 nm have been doped with 10% MoO$_x$ for improvement of the conductivity.

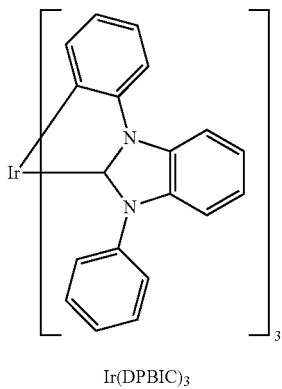

Ir(DPBIC)$_3$ (For the preparation of Ir(DPBIC)3 see Ir complex (7) in the application PCT/EP/04/09269).

Thereafter, a mixture of 20% di-[1,3,5-triphenyl-1,3,4-triazol-2-yliden-C2,C2']platin(II)di-pyrazolat (1c'), 60% Ma A and 20% of the compound Ir(DPBIC)$_3$ is applied by vapor deposition in a thickness of 20 nm.

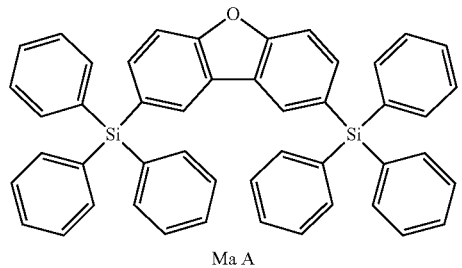 [SMILES: c1ccc([Si](c2ccccc2)(c2ccccc2)c2ccc3oc4ccc([Si](c5ccccc5)(c5ccccc5)c5ccccc5)cc4c3c2)cc1]

Ma A (For the preparation of Ma A see WO2009003898)

Thereafter, a 10 nm-thick layer of Ma A as hole and exciton blocker is applied. The subsequent electron conductor layer used is a Cs$_2$CO$_3$-doped BCP layer with a layer thickness of 30 nm. An aluminum cathode of thickness 100 nm concludes the diode.

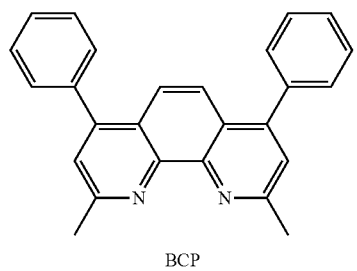

BCP

All components are adhesive bonded to a glass lid in an inert nitrogen atmosphere.

Diode Example 2

The light emitting layer following the hole injection layer is also applied from solution. Therefore, a solution comprising 12.5 mg solids per 1 ml of the solvent toluene is prepared. The solids content consists of 10% di-[1-(dibenzofuranyl)-3-methylimidazol-2-yliden-C2,C2']platin(II)di-pyrazolat (1a'), 30% of the matrix Ir(DPBIC)$_3$ and 60% of Ma A.

After the light emitting layer, the organic materials specified below are applied to the layers applied from solution by vapor deposition at a rate of approx. 0.5-5 nm/min to the clean substrate at about $10^{-7}$-$10^{-9}$ mbar. As hole and exciton blocker Ma A is applied in a thickness of 10 nm.

The subsequent electron conductor layer used is a Cs$_2$CO$_3$-doped BCP layer with a layer thickness of 30 nm. An aluminum cathode of thickness 100 nm concludes the diode.

All components are adhesive bonded to a glass lid in an inert nitrogen atmosphere.

To characterize the OLED, electroluminescence spectra are recorded at different currents and voltages. In addition, the current-voltage characteristic is measured in combination with the light output emitted. The light output can be converted to photometric parameters by calibration with a photometer.

For the two blue example diodes, the following electrooptical data are obtained:
Diode example 1: CIE (0.17; 0.21), maximum EQE* 8.3%
Diode example 2: CIE (0.179; 0.34)
*EQE—external quantum efficiency. Measured in the forward direction assuming a Lambertian light intensity distribution.

The invention claimed is:
1. A dinuclear Pt-carbene complex of formula (Ia) or (Ib) or an isomer thereof:

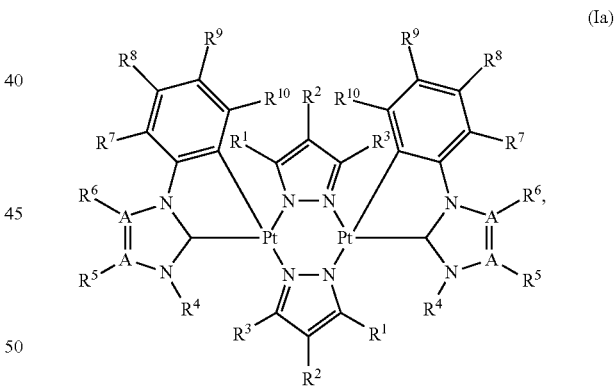

(Ia)

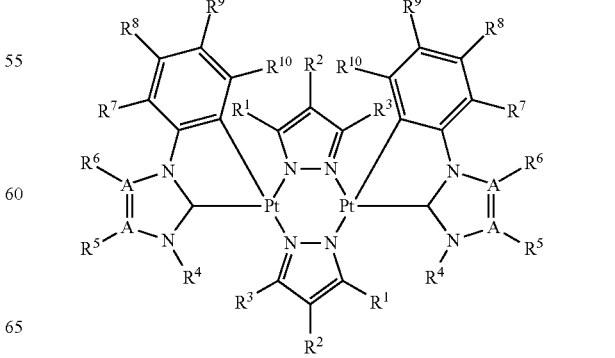

(Ib)

wherein each A is independently N or C, each $R^1$, $R^2$, and $R^3$ is independently hydrogen; a linear or branched alkyl radical having from 1 to 20 carbon atoms, optionally interrupted by at least one heteroatom and optionally bearing at least one functional group; or a cycloalkyl radical having from 3 to 20 carbon atoms, each $R^4$ is independently a linear or branched alkyl radical having from 1 to 20 carbon atoms, optionally interrupted by at least one heteroatom and optionally bearing at least one functional group; a cycloalkyl radical having from 3 to 20 carbon atoms; a substituted or unsubstituted aryl radical having from 6 to 30 carbon atoms; or a substituted or unsubstituted heteroaryl radical having a total of from 5 to 18 carbon atoms and heteroatoms, each $R^5$ and $R^6$, if an adjacent A is N, is a free electron pair, each $R^5$ and $R^6$, if an adjacent A is C, is independently hydrogen; a linear or branched alkyl radical having from 1 to 20 carbon atoms, optionally interrupted by at least one heteroatom and optionally with at least one functional group; a cycloalkyl radical having from 3 to 20 carbon atoms; a substituted or unsubstituted aryl radical having from 6 to 30 carbon atoms; a substituted or unsubstituted heteroaryl radical having a total of from 5 to 18 carbon atoms and heteroatoms, $R^4$ and $R^5$, or $R^5$ and $R^6$ optionally form a saturated, unsaturated, or aromatic ring, optionally interrupted by a heteroatom, and having a total of from 5 to 18 carbon atoms and heteroatoms, each $R^7$, $R^8$, $R^9$, and $R^{10}$ is independently hydrogen; a linear or branched alkyl radical having from 1 to 20 carbon atoms, optionally interrupted by at least one heteroatom and optionally bearing at least one functional group; a cycloalkyl radical having from 3 to 20 carbon atoms; a substituted or unsubstituted aryl radical having from 6 to 30 carbon atoms; a substituted or unsubstituted heteroaryl radical having a total of from 5 to 18 carbon atoms and heteroatoms; an ether functional group; an amino functional group; a thio functional group; an ester functional group; a carbonyl functional group; a nitro functional group; or a halogen group, $R^7$ and $R^8$, $R^8$ and $R^9$, and $R^9$ and $R^{10}$ each optionally form a saturated, unsaturated, or aromatic, optionally substituted ring, optionally interrupted by a heteroatom, and having a total of from 5 to 18 carbon atoms and heteroatoms, and $R^6$ and $R^7$ optionally form a saturated or unsaturated, linear or branched bridge optionally comprising a heteroatom, having a total of from 1 to 30 carbon atoms and heteroatoms, optionally further comprising an aromatic unit, a heteroaromatic unit or functional group, or a combination thereof, and optionally fused with a substituted or unsubstituted five- to eight-membered ring comprising a carbon atom, a heteroatom, or both.

2. The dinuclear Pt-carbene complex of claim 1, wherein each $R^1$ and $R^3$ is independently hydrogen or a linear or branched alkyl radical having from 1 to 4 carbon atoms, $R^2$ is hydrogen, each $R^4$ is independently a linear or branched alkyl radical having from 1 to 4 carbon atoms; a substituted or unsubstituted aryl radical having 6 carbon atoms; or a substituted or unsubstituted heteroaryl radical having a total of 5 carbon atoms and heteroatoms, each $R^5$ and $R^6$, if an adjacent A is N, is a free electron pair, each $R^5$ and $R^6$, if an adjacent A is C, is independently hydrogen; a linear or branched alkyl radical having from 1 to 4 carbon atoms; a substituted or unsubstituted aryl radical having 6 carbon atoms; or a substituted or unsubstituted heteroaryl radical having a total of 5 carbon atoms and heteroatoms, $R^5$ and $R^6$ optionally form an aromatic ring optionally interrupted by a heteroatom, having a total of from 5 to 10 carbon atoms and heteroatoms, and each $R^7$, $R^8$, $R^9$, and $R^{10}$ is independently hydrogen, with the proviso that $R^7$ and $R^8$ optionally instead form an optionally substituted unsaturated or aromatic ring, optionally interrupted by a heteroatom, having a total of from 5 to 12 carbon atoms and heteroatoms.

3. The dinuclear Pt-carbene complex of claim 1 of any of formulae (Ia), (Ib), (Ic), (Id), (Ie), and (If), or an isomer thereof:

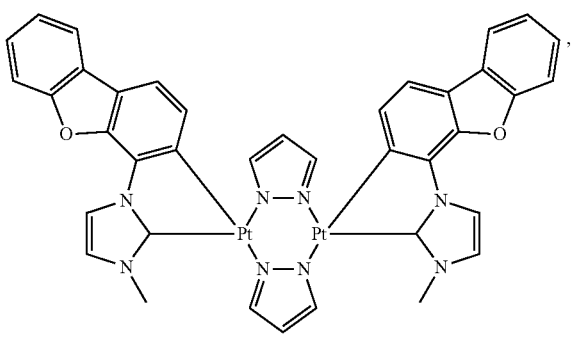

(Ia)

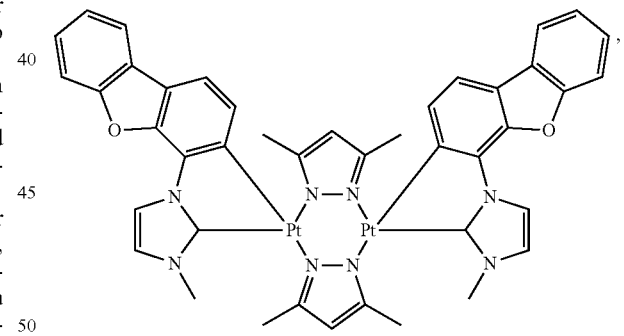

(Ib)

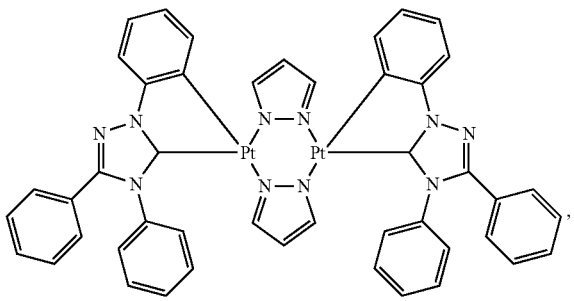

(Ic)

-continued (Id)
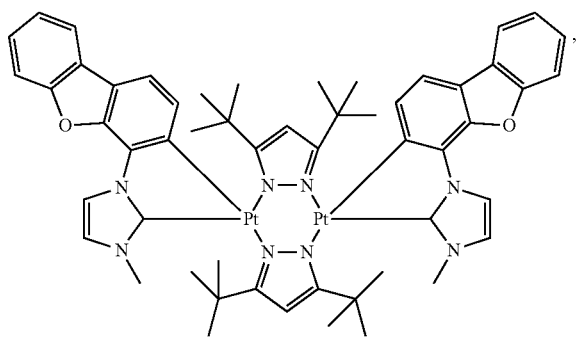

(Ie)
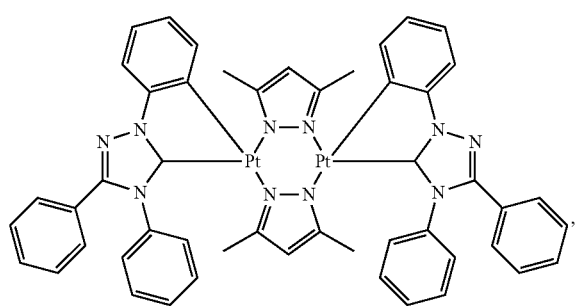

(If)
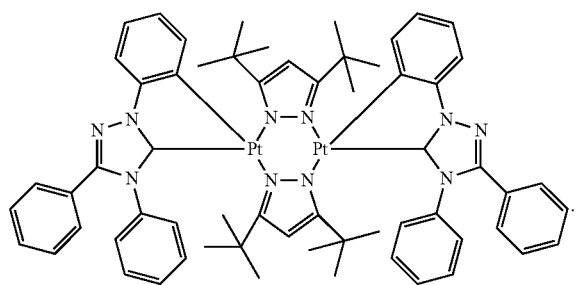

4. The dinuclear Pt-carbene complex of claim 1, wherein an $R^6$ and an $R^7$ form a phenyl ring.

5. An organic electronic component comprising the dinuclear Pt-carbene complex of claim 1.

6. The organic electronic component of claim 5,
wherein the organic electronic component is an organic light-emitting diode (OLED), an organic photovoltaic cell (OPV), an organic field-effect transistor (OFET), or a light-emitting electrochemical cell (LEEC).

7. A device comprising the organic electronic component of claim 6,
wherein the organic electronic component is an OLED, and the device is selected from the group consisting of a stationary visual display unit, a mobile visual display unit, and an illumination device.

8. A light-emitting layer comprising the dinuclear Pt-carbene complex of claim 1.

9. An organic light-emitting diode (OLED) comprising the light-emitting layer of claim 8.

10. A device, comprising the OLED of claim 9,
wherein the device is selected from the group consisting of a stationary visual display unit, a mobile visual display unit, and an illumination device.

11. An OLED, comprising:
an emitter, a matrix material, a charge transport material, or a charge blocker, comprising the dinuclear Pt-carbene complex of claim 1.

12. A process for preparing the dinuclear Pt-carbene complex of claim 1, comprising: contacting a Pt compound with a corresponding ligand, a corresponding ligand precursor, a pyrazole, a corresponding pyrazole derivative, or a combination thereof.

13. The process of claim 12, comprising:
contacting the Pt compound with a corresponding ligand precursor of formula (III):

(III)
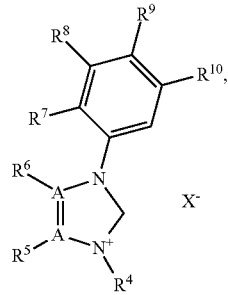

wherein $X^-$ is a halide, $BF_4^-$, $PF_6^-$, $SbF_6^-$, $ClO_4^-$, or $½SO_4^{2-}$.

14. The process of claim 13, wherein $X^-$ is chloride, bromide, iodide, $BF_4^-$, or $PF_6^-$.

15. The process of claim 14, wherein $X^-$ is iodide.

16. The process of claim 15, wherein the corresponding ligand precursor is of formula (IIIa) or (IIIb):

(IIIa)
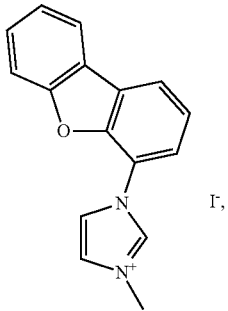

(IIIb)
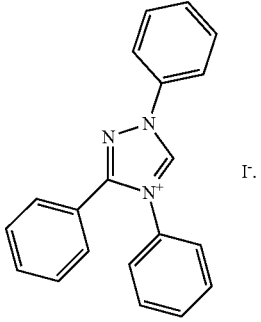

17. The process of claim 12, comprising:
contacting the Pt compound with a pyrazole or corresponding pyrazole derivative of formula (IV1) or (IV2):
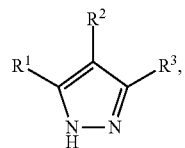
(IV1)
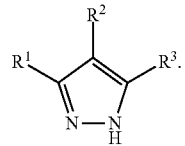
(IV2)
18. The process of claim 17, wherein the pyrazole or corresponding pyrazole derivative is any of compounds (IVa), (IVb), (IVc), (IVd), (IVe), and (IVf):
(IVa)
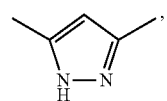
(IVb)
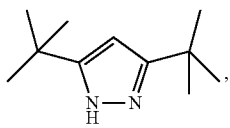
(IVc)
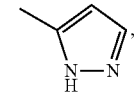
(IVd)
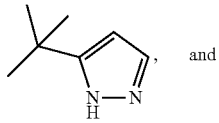
(IVe)
and
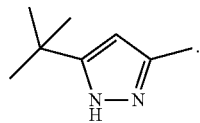
(IVf)
* * * * *